United States Patent [19]

Leonard

[11] 4,286,951
[45] Sep. 1, 1981

[54] DENTAL HANDPIECE
[75] Inventor: Henri Leonard, Besancon, France
[73] Assignee: Micro Mega, S.A., France
[21] Appl. No.: 98,617
[22] Filed: Nov. 29, 1979
[30] Foreign Application Priority Data
Dec. 27, 1978 [FR] France ............................. 78 37117
[51] Int. Cl.³ ..................... A61C 1/08; A61C 1/12; A61C 1/05
[52] U.S. Cl. .................................. 433/126; 433/133
[58] Field of Search ............................ 433/126, 133
[56] References Cited
U.S. PATENT DOCUMENTS
2,701,147  2/1955  Summerville .................... 433/126
4,211,009  7/1980  Leonard ........................... 433/126

Primary Examiner—Robert Peshock
Attorney, Agent, or Firm—Robert E. Burns; Emmanuel J. Lobato; Bruce L. Adams

[57] ABSTRACT

In a dental handpiece, in particular a contra-angle, comprising a head and a handle coupled with a bayonet joint, an internal support for a tool-driving shaft fits freely in the head and has a rear portion fitting freely in the handle. In the vicinity of the coupling between the head and handle, the internal support has an enlargement providing a forwardly facing shoulder and a rearwardly facing shoulder. A groove at the base of the forwardly facing shoulder receives an O-ring. When the head and handle are coupled, the enlargement and O-ring are clamped between internal shoulders in the head and handle to position the internal support and restrain it from rotating.

5 Claims, 2 Drawing Figures

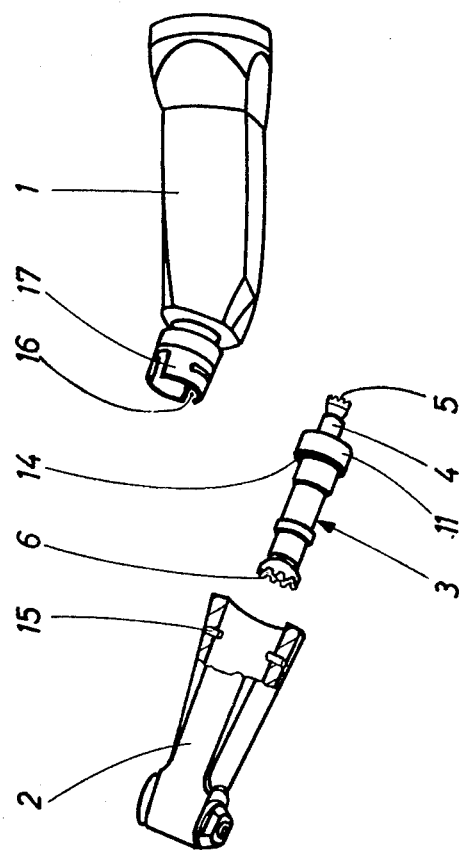

DENTAL HANDPIECE

BACKGROUND OF THE INVENTION

This invention relates to a dental handpiece comprising essentially a rear portion or handle and a front portion or head, means for detachably coupling these two portions with each other, which consist of a bayonet system formed on either of the portions, an internal support mounted in the head and handle and adapted to receive the tool driving shaft, and means for fastening said internal support to the head and handle portions.

DESCRIPTION OF THE PRIOR ART

Dental handpieces of this type are well known in the art, wherein the internal support is secured to the head of the handpiece by means of a small screw passing through a hole formed in the lower face of the head and engaging a tapped hole formed in the internal support. Though this fastening method is fully satisfactory as far as its efficiency is concerned, it is objectionable in that when the surgeon-dentist wants to disassemble the handpiece he must use a screwdriver.

SUMMARY OF THE INVENTION

The purpose of the present invention is to provide a dental handpiece which can easily be assembled as disassembled without using a screwdriver.

For this purpose, the handpiece according to this invention is characterised in that the internal support is an easy and free fit in the handle, the head body being likewise an easy and free fit on said internal support, and that said fastening means consists of a base portion formed on said internal support and adapted to be clamped longitudinally between two inner abutment means formed in the head body and at the front end of the handle, respectively, an O-ring being disposed between these three elements for reducing or preventing the rotation of the internal support.

With this arrangement a handpiece permitting a quick assembling of its component elements is obtained while preserving the necessary high degree of rigidity of these elements when the two portions of the handpiece are locked to each other.

A preferred and exemplary form of embodiment of the dental handpiece according to the instant invention will now be described in detail with reference to the accompanying drawing.

BRIEF DESCRIPTION OF THE DRAWING

FIG. 2 is an exploded perspective view of the same handpiece.

DESCRIPTION OF THE PREFERRED EMBODIMENT

Figure 1:
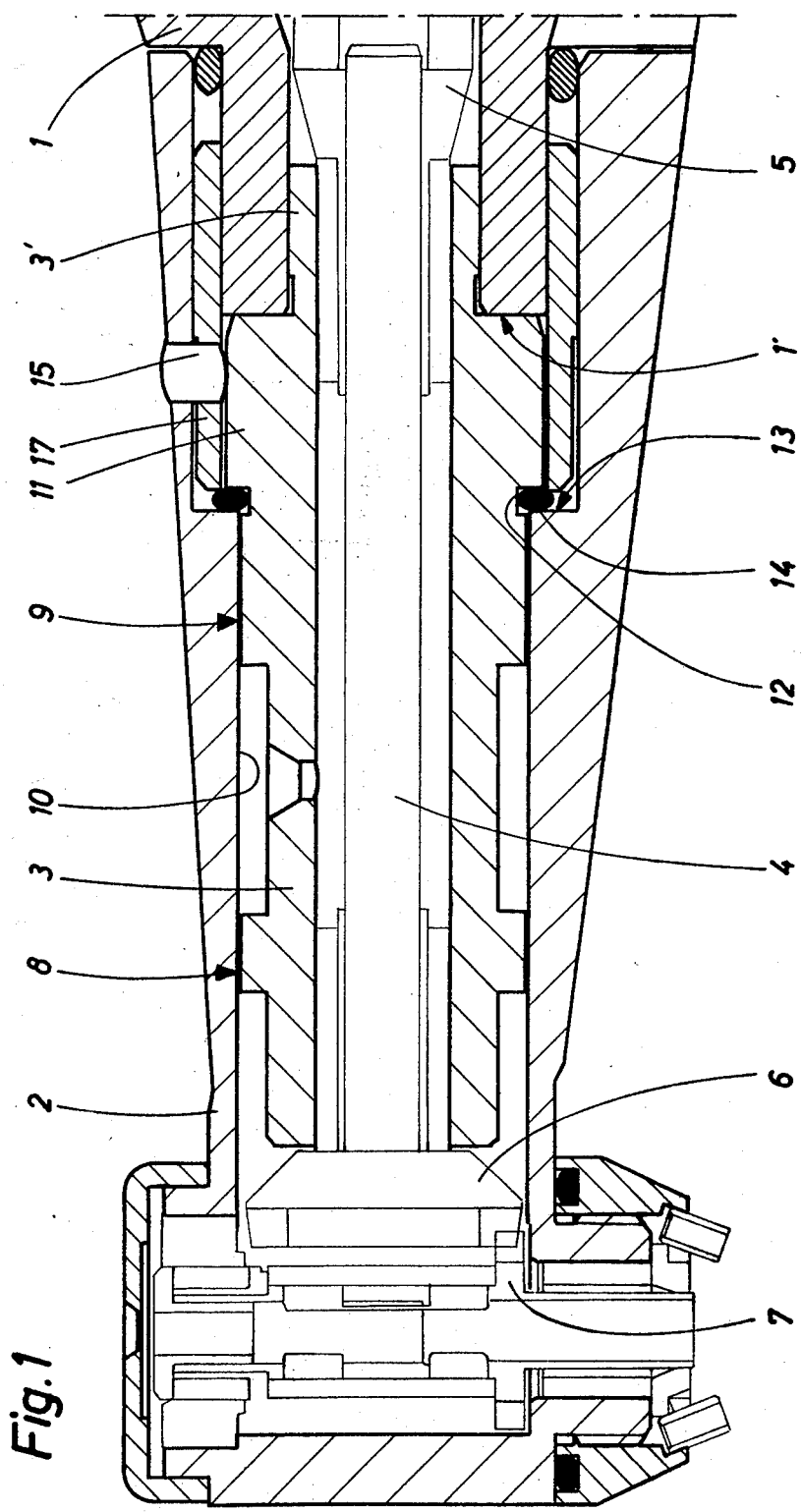
FIG. 1 is a longitudinal axial section showing on a large scale the handpiece of this invention.

The dental handpiece according to this invention comprises three sections, namely a rear section 1 constituting a handle, a front section 2 or head in which the tool (not shown) is to be inserted, and an internal support or socket 3 in which the central rotary shaft 4 for driving the tool is rotatably mounted. The rear end 5 of the central shaft 4 is driven in a manner known per se by the output shaft of, or coupled to, the motor (not shown), and the front end of this shaft 4 carries a pinion 6 driving also in a known fashion the tool clamping means or mandrel 7.

The internal support or socket 3 has two outer and longitudinally spaced peripheral journal lands 8 and 9 formed thereon on which the head body 2, provided for this purpose with a cylindrical bore 10, is an easy fit. The rear end 3' of the internal support 3 is also fitted freely in the front end of the handle portion 1. The internal support 3 further comprises an enlarged cylindrical base portion 11 adjacent the rear end 3' fitted in the handle, and an annular groove 12 is formed in the surface of the internal support 3 adjacent the front annular surface of the base portion 11 which faces the head of the handpiece. When these component elements are assembled, the base portion 11 is clamped between the end face 1' of handle 1 and an annular inner shoulder 13 formed in the inner bore 10 of the head body 2. An O-ring 14 is fitted in the annular groove 12 and thus compressed between the shoulder 13 and the registering front face of base member 11, to prevent the internal support 3 from rotating in the handpiece.

The head body 2 is coupled to the front end of handle 1 by means of a bayonet locking device comprising a pair of radial pins 15 fitted in the head body 2 and adapted to engage a pair of corresponding L-shaped slots 16 formed in a socket 17 force fitted to the end of handle 1. Preferably, the pair of pins or the pair of corresponding L-shaped slots are not diametrally opposed in order to provide a single locking position.

Thus, when the three sections are fitted into one another and locked by means of the above-described bayonet locking device, the O-ring 14 is firmly compressed between the three elements, the resilient friction thus created safely preventing any rotation of the internal support 3 within the handpiece. As already explained in the foregoing, this arrangement permits of easily disassembling the handpiece without resorting to a screwdriver or any other specific tool means.

This device is particularly adequate for bent or contra-angle handpieces; however, it is also advantageously applicable to straight handpieces.

What is claimed is:

1. A dental handpiece comprising a rear portion or handle and a front portion or head, means comprising a bayonet joint for coupling said handle and head together end-to-end, an internal support fitting freely in said head and having a rear portion extending freely into said handle, a tool-driving shaft rotatably supported in said internal support, said internal support having in the vicinity of the junction between said head and handle an enlargement defining a forwardly facing shoulder and a rearwardly facing shoulder, and an annular groove at the base of said forwardly facing shoulder, an O-ring received in said groove and against said forwardly facing shoulder, said handle having an internal shoulder engageable with said rearwardly facing shoulder of said enlargement, and said head having an internal shoulder engageable with said O-ring, said enlargement and O-ring being clamped between said internal shoulders of said handle and head when said handle and head are coupled by said bayonet joint to position said internal support longitudinally in said head and handle and to restrain it against rotation.

2. A dental handpiece according to claim 1, in which said internal support has two longitudinally spaced lands which fit freely in said head.

3. A dental handpiece according to claim 2, in which said enlargement is formed on one of said lands.

4. A dental handpiece according to claim 1, in which said bayonet joint comprises a socket force-fitted on the forward end of said handle and having L-shaped slots in its forward edge and radial pins on said head engageable in said slots.

5. A dental handpiece according to claim 4, in which said L-shaped slots and said pins are disposed out of diametrical alignment with one another.

* * * * *